(12) United States Patent
Urban et al.

(10) Patent No.: US 8,997,556 B2
(45) Date of Patent: Apr. 7, 2015

(54) APPARATUS FOR DETERMINING AND/OR MONITORING A PROCESS VARIABLE

(75) Inventors: Martin Urban, Lorrach (DE); Serguej Lopatin, Lorrach (DE); Helmut Pfeiffer, Steinen (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 752 days.

(21) Appl. No.: 13/140,174

(22) PCT Filed: Dec. 11, 2009

(86) PCT No.: PCT/EP2009/066908
§ 371 (c)(1),
(2), (4) Date: Jun. 16, 2011

(87) PCT Pub. No.: WO2010/069866
PCT Pub. Date: Jun. 24, 2010

(65) Prior Publication Data
US 2012/0103088 A1     May 3, 2012

(30) Foreign Application Priority Data
Dec. 19, 2008    (DE) .................. 10 2008 054 945

(51) Int. Cl.
G01N 29/02      (2006.01)
G01F 23/296     (2006.01)
(52) U.S. Cl.
CPC ................................ *G01F 23/2967* (2013.01)
(58) Field of Classification Search
USPC .......... 73/290 V, 32 A, 54.26, 54.27
See application file for complete search history.

(56) References Cited

U.S. PATENT DOCUMENTS

| 3,139,544 A | 6/1964 | Tomes |
| 4,540,981 A | 9/1985 | Lapetina |
| 4,875,362 A | 10/1989 | Skallen |
| 2004/0093941 A1* | 5/2004 | Lopatin ...................... 73/290 V |

FOREIGN PATENT DOCUMENTS

| DE | 33 36 991 A1 | 5/1985 |
| DE | 36 43 349 A1 | 7/1987 |
| DE | 38 10 669 A1 | 10/1989 |

(Continued)

OTHER PUBLICATIONS

German Search Report.

(Continued)

*Primary Examiner* — Paul West
(74) *Attorney, Agent, or Firm* — Bacon & Thomas, PLLC

(57) ABSTRACT

An apparatus for determining and/or monitoring at least one process variable of a medium. The apparatus includes: at least one mechanically oscillatable unit, which comes in contact at least partially with the medium; at least one transducer unit, which excites the mechanically oscillatable unit to execute mechanical oscillations and which receives mechanical oscillations from the mechanically oscillatable unit; and at least one housing. At least one limiting element is provided. The limiting element is embodied and arranged in such a manner that the limiting element at least partially surrounds the mechanically oscillatable unit and the therefrom resulting reduction of volume surrounding the mechanically oscillatable unit increases the measuring sensitivity of the apparatus. Furthermore, the invention relates to a limiting element.

14 Claims, 5 Drawing Sheets

(56) References Cited

FOREIGN PATENT DOCUMENTS

| | | |
|---|---|---|
| DE | 42 33 185 C1 | 1/1994 |
| DE | 38 78 473 T3 | 6/2001 |
| DE | 10 2004 055 552 A1 | 5/2006 |
| DE | 10 2005 053 331 A1 | 5/2007 |
| DE | 10 2006 007 199 A1 | 8/2007 |
| GB | 1 554 726 | 10/1979 |
| WO | WO 02/079733 A1 | 10/2002 |

OTHER PUBLICATIONS

International Search Report.
English translation of the IPR.
Cherian, A: "Apparatus for sensing the level of particulate matter or liquid relative to a preselected level in a container", Xerox Disclosure Journal, Stamford, Connecticut, Bd. 19, Nr. 5, Sep. 1, 1994.

* cited by examiner a)

b)

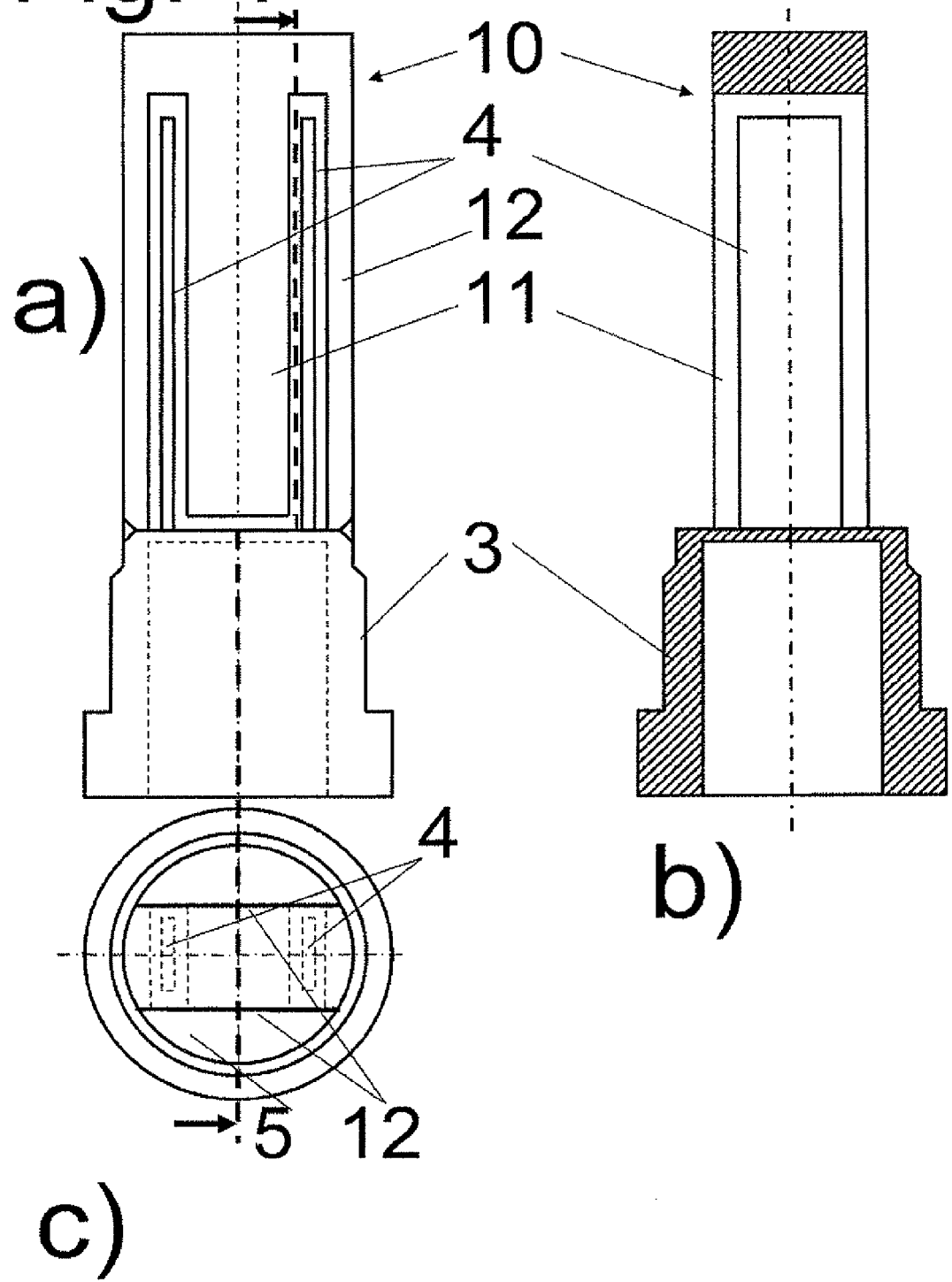

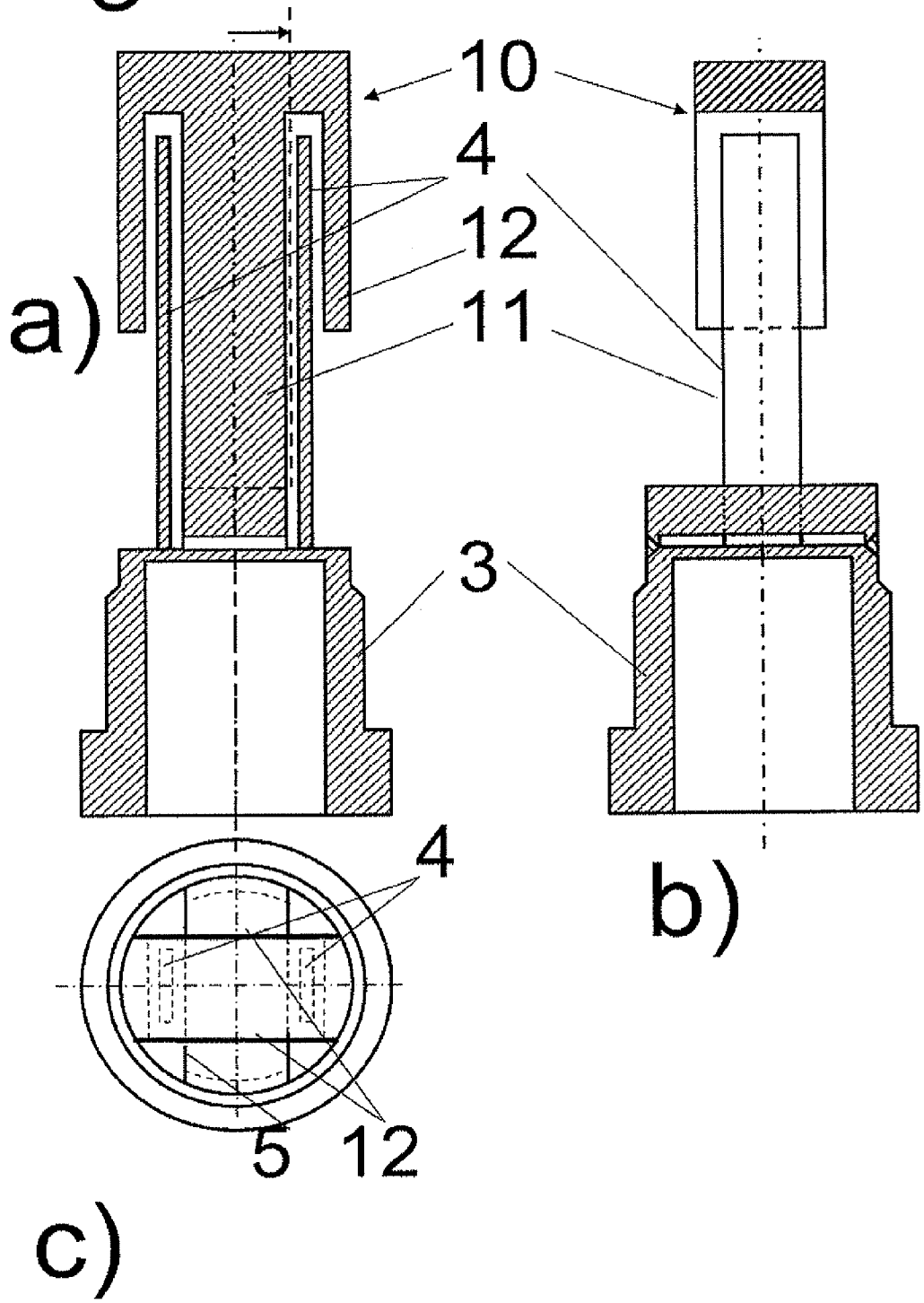

APPARATUS FOR DETERMINING AND/OR MONITORING A PROCESS VARIABLE

TECHNICAL FIELD

The invention relates to an apparatus for determining and/or monitoring at least one process variable of a medium. The apparatus includes: at least one mechanically oscillatable unit, which comes in contact at least partially with the medium; at least one transducer unit, which excites the mechanically oscillatable unit to execute mechanical oscillations and which receives mechanical oscillations from the mechanically oscillatable unit; and at least one housing. Furthermore, the invention relates to a limiting element for an apparatus for determining and/or monitoring at least one process variable of a medium, wherein the apparatus includes: At least one mechanically oscillatable unit, which comes at least partially in contact with the medium; and at least one housing. The process variable is, for example, the fill level, density or viscosity of the medium, which, for example, is a liquid, a gas or a bulk good.

BACKGROUND DISCUSSION

So called oscillatory forks (e.g. EP 0 444 173 B1), single rods (e.g. WO 2004/094964 A1) or also membrane oscillators are known from the state of the art for determining fill level and other process variables of a medium. The characterizing variables of the mechanical oscillations (oscillation amplitude, resonance frequency, phase response as a function of frequency) of the oscillatable unit depend on contact with the medium and also its properties. This is exploited for the various measurements. Thus for example, the frequency or the amplitude of the oscillations decreases especially when a liquid medium reaches and at least partially covers the oscillatable unit. On the one hand, the liquid medium acts on the oscillating body of the sensor, that is. e.g. the oscillatory fork, the single rod, or the membrane, as a co-moving mass, so that the oscillation frequency sinks, and, on the other hand, as a mechanical damper, so that the oscillation amplitude decreases. Therefore, it can be ascertained from the decrease of the oscillation frequency or amplitude, dependent on the embodiment and the position of the application of the apparatus, that the medium has reached a fill level. Furthermore, the oscillation frequency is also dependent, for example, on the viscosity of the medium (see e.g. EP 1 325 301). Such measuring devices are most often excited to the resonance frequency oscillations by means of an electromechanical transducer.

Frequently, these sensors are used as limit level switches. If the process variable is, for example, the fill level, then the sensor produces a signal, which displays that the fill level, which is predetermined by the embodiment of the sensor and its location of mounting, was reached or subceeded (fallen beneath).

In the use of oscillatory forks in liquids with low density (e.g. smaller than 0.5 g/cm$^3$ such as liquefied gases), the frequency difference between the oscillation frequency in air and the oscillation frequency in the immersed state is usually too small for an assured evaluation. The temperature and the process pressure influence especially the oscillation frequency in similar orders of magnitude as a frequency change as a result of a change of the density of the medium. In other words: the density sensitivity of the sensor can be too small in such cases in comparison to disturbing influences such as temperature or density.

SUMMARY OF THE INVENTION

Therefore, an object of the invention is to increase the density sensitivity of the oscillatable sensor, especially for application with very light liquids.

On the one hand, the invention achieves the object by an apparatus for determining and/or monitoring at least one process variable of a medium. On the other hand, the invention achieves the object by a limiting element for an apparatus for determining and/or monitoring of at least one process variable of a medium. Thus, for example, an apparatus according to the state of the art can be developed into an apparatus of the invention by incorporation of the limiting element of the invention.

The invention achieves the object by an apparatus for determining and/or monitoring at least one process variable of a medium, wherein the apparatus includes: At least one mechanically oscillatable unit, which comes at least partially in contact with the medium; at least one transducer unit, which excites the mechanically oscillatable unit to execute mechanical oscillations and which receives mechanical oscillations from the mechanically oscillatable unit; and at least one housing. The apparatus is embodied, in such case, in such a manner that at least one limiting element is provided, and the limiting element is embodied and arranged in such a manner that the limiting element at least partially surrounds the mechanically oscillatable unit and the reduction of volume surrounding the mechanically oscillatable unit resulting therefrom increases the measuring sensitivity of the apparatus. The limiting element is, in such case, either a permanently applied limiting element or, in given cases, an only temporarily securable element, which, for example, is appliable to a measuring device already assembled and corresponding to the state of the art. The apparatus is one of the measuring devices from the state of the art previously described, for example, an oscillatory fork, a single rod, or a membrane oscillator.

The volume around the oscillatory elements is lessened by the limiting element. Through this the frequency change, i.e. the change of the frequency as a result of the change of the process variable, increases as a result of additional interaction forces acting in the gap between the wall and the oscillatory elements. According to the invention, the measuring sensitivity is increased by the feature that the volume around the mechanically oscillatable unit is purposely limited to a well defined degree or is at least reduced. Expressed in another way, the co-moving mass is increased by limiting of the volume around the mechanically oscillatable unit and thereby influences the resonance behavior of the oscillatable unit.

A transducer for liquids, wherein the transducer has a fork shaped oscillatable unit, is known from DE 3878473 T3. This transducer optionally has a solid or a wire weave, cylindrical protective sleeve, which surrounds the oscillatable unit. The protective sleeve there described serves, however, only for the protection of the oscillatable unit from possibly present particles, which could otherwise damage it. This is in contrast to the limiting element of the invention. In the case of this prior sensor, sensitivity is achieved in another way, for example, by a re-entry surface in the fork tines.

An embodiment of the apparatus of the invention provides that the mechanically oscillatable unit has at least two fork tines. The oscillatable unit is, thus, an oscillatory fork, in which two fork tines are placed on a membrane, via which the oscillation transmission to the transducer unit which, for example, has at least one piezoelectric element, preferably takes place.

An embodiment of the apparatus of the invention provides that the mechanically oscillatable unit has at least one membrane. In this embodiment, the mechanically oscillatable unit is, for example, a pure membrane oscillator, i.e. the mechanically oscillatable unit comprises only the membrane, or the membrane is mechanically coupled to additional elements, e.g. the two fork tines mentioned above.

An embodiment of the apparatus of the invention provides that the mechanically oscillatable unit has at least one paddle. In some embodiments, single rods or oscillatory forks have a paddle on its rods or tines. The paddle is an areal element, which increases the effective area.

An embodiment of the apparatus of the invention provides that the limiting element has at least one plate and that the plate is arranged between the at least two fork tines of the mechanically oscillatable unit. This plate thus limits in one direction the medium, which comes in contact with the oscillatable unit. Depending on the embodiment this results in a kind of partition.

An embodiment of the apparatus of the invention provides that the limiting element has at least one pot like element with an inner space open on at least one side and that the inner space of the pot like element surrounds at least one part of the mechanically oscillatable unit. In this embodiment, thus, the oscillatable unit is partially surrounded by the limiting element, so that at least in certain regions, the amount of fluid that surrounds the oscillatable unit is determined by the internal volume of the pot like element.

An embodiment of the apparatus of the invention provides that the inner space of the pot like element surrounds at least the paddle of the mechanically oscillatable unit. In this embodiment, the region of the oscillatable unit, which has an especially enlarged effective area due to the paddle shape, is at least surrounded by the pot like element.

An embodiment of the apparatus of the invention provides that the pot like element has at least one traversing cavity. The traversing cavity serves for flow of the medium, so that the medium can penetrate the inner space of the pot like element and, in given cases, be replaced by new medium. There can also be a number of cavities present, which enable inflow or outflow. The cavity or cavities can be holes or slits located on the side of or in the floor of the pot like element.

An embodiment of the apparatus of the invention provides that the limiting element is embodied and connected with the housing in such a manner that the mechanically oscillatable unit is essentially free from direct mechanical contact with the limiting element.

An embodiment of the apparatus of the invention provides that the limiting element is at least partially placed at an edge of the membrane. Since the limiting element should essentially not influence the actual mechanical oscillations, the limiting element is placed outside the region of active oscillation of the membrane.

An embodiment of the apparatus of the invention provides that the plate of the limiting element is embodied in such a manner, and the limiting element is connected to the edge of the membrane in such a manner, that the membrane is free from direct mechanical contact with the plate.

Furthermore, the invention achieves the object through a limiting element for an apparatus for determining and/or monitoring at least one process variable of a medium, wherein the apparatus has at least one mechanically oscillatable unit, which comes at least partially in contact with the medium; and wherein the apparatus has at least one housing. The limiting element of the invention is characterized in that the limiting element is embodied and is arrangeable relative to the mechanically oscillatable unit in such a manner that the limiting element at least partially surrounds the mechanically oscillatable unit and affects an increase in the measuring sensitivity of the apparatus. Thus, the invention also achieves the object by a limiting element, which serves as a supplemental element for developing a measuring device of the state of the art into a measuring device of the invention. The region around the mechanically oscillatable unit is bordered by this limiting element. Furthermore, the explanations set forth above and the corresponding embodiments also hold here. Thus, in given cases, a well defined measurement volume around the mechanically oscillatable unit results from the limiting element. The limiting element is embodied, in such case, for example, in such a manner that it is appliable to measuring devices already existing or that it is installed during the manufacture of a measuring apparatus.

An embodiment of the limiting element of the invention provides that the limiting element has at least one plate.

An embodiment of the limiting element of the invention provides that the limiting element has at least one pot like element with an inner space open on at least one side.

An embodiment of the limiting element of the invention provides that the limiting element is embodied and is connectable to the housing in such a manner that the mechanically oscillatable unit is essentially free from direct mechanical contact with the limiting element.

An embodiment of the limiting element of the invention provides that the limiting element is at least partially placeable on an edge of the membrane.

An embodiment of the limiting element of the invention provides that the plate of the limiting element is embodied in such a manner and that the limiting element is connectable to the edge of the membrane in such a manner that the membrane is free from direct mechanical contact with the plate.

BRIEF DESCRIPTION OF THE DRAWINGS

The invention will now be explained in greater detail based on the appended drawing, the figures of which show as follows:

FIG. 5a), FIG. 5b) and FIG. 5c)—are three sections through another embodiment of an oscillatory fork of the invention.

DETAILED DISCUSSION IN CONJUNCTION WITH THE DRAWINGS

Figure 1:
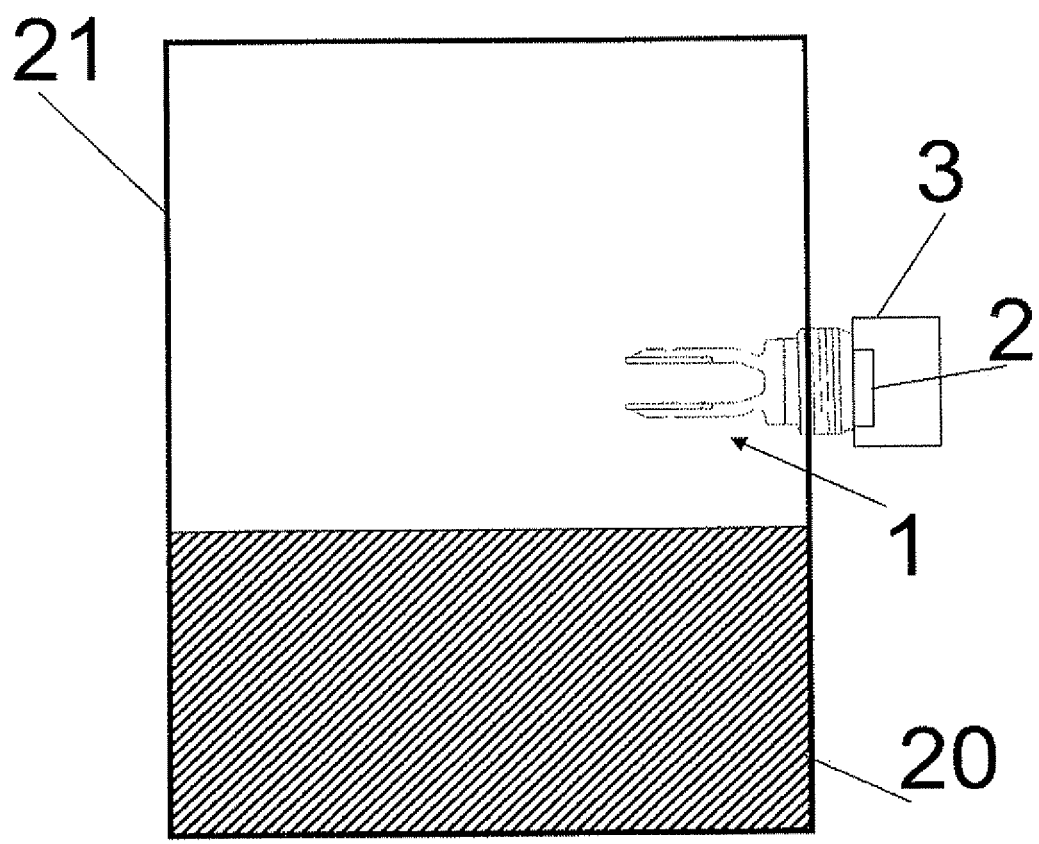
FIG. 1—is a schematic representation of the application of a limit level switch, FIG. 2—is a three-dimensional representation of an oscillatory fork of the invention, FIG. 3a) and FIG. 3b)—are two sections through the oscillatory fork of FIG. 2, FIG. 4a), FIG. 4b) and FIG. 4c)—are three sections through another embodiment of an oscillatory fork of the invention.

An example of a sensor used as a limit level switch is shown in FIG. 1. The mechanically oscillatable unit 1 is, in such case, referred to as an oscillatory fork, in which case two fork tines are secured to a membrane. The fork tines here reach into the inner space of the container 21, where the medium 20 is located. The medium 20 is, for example, a liquid. It is to be noted that the invention concerns, in addition to the illustrated oscillatory fork, also measuring devices using a single rod oscillator or a membrane oscillator as the mechanically oscillatable unit. A large variety of such measuring devices are available from the assignee. If the medium 20 reaches the mechanically oscillatable unit 1, it influences the oscillations of the mechanically oscillatable unit 1, which is shown, for example, as a change in the frequency and/or the amplitude. The interaction between the medium 20 and the mechanically oscillatable unit 1 also permits, in such case, the determining or monitoring of process variables such as density or viscosity for example; wherein with these measurements, the degree of covering by the medium should be known.

The housing 3, in which the transducer unit 2 and, for example, also the electronics, which provides for the feedback and for processing the oscillations, is located, is here located outside the container 21. In such case, the transducer unit 2 excites the mechanically oscillatable unit 1 to execute oscillations based on an exciter signal and receives the mechanical oscillations of the mechanically oscillatable unit 1, which it converts into a received signal.

Figure 2:
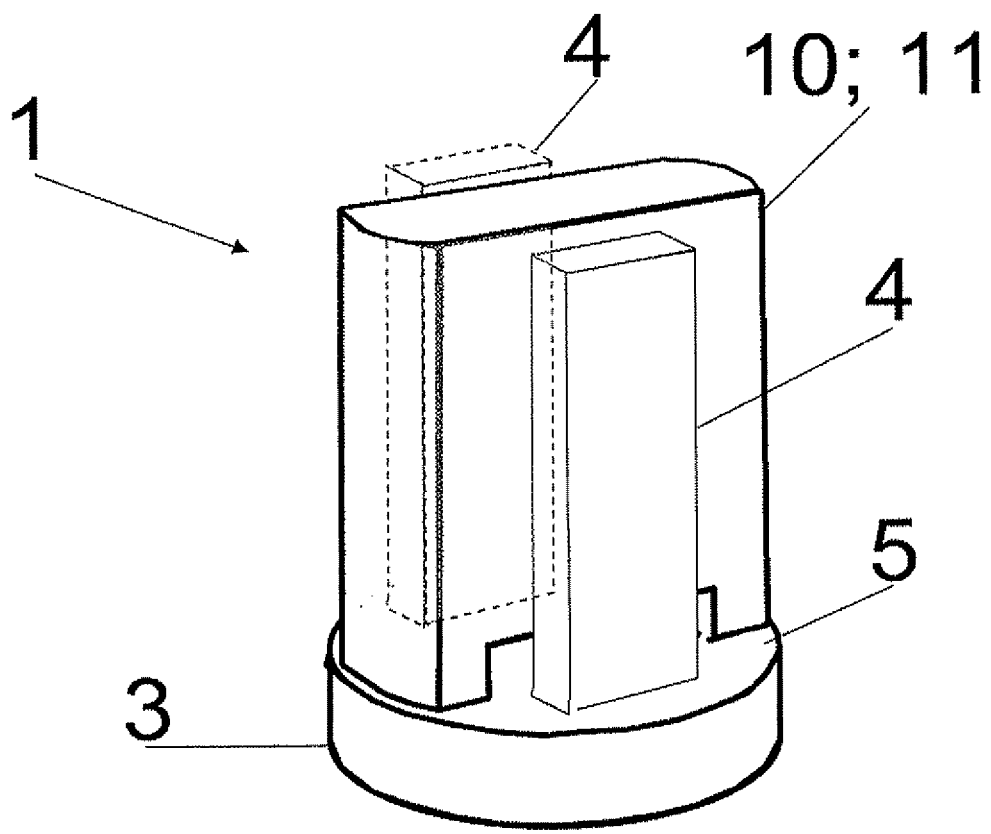

FIG. 2 shows a part of a measuring device of the invention. Here, a limiting element 10, which is arranged as a plate 11 between the two fork tines 4, is provided for increasing the accuracy of measurement, e.g. for determining and/or monitoring the density of the medium. The two fork tines 4 are secured to the membrane 5 so that a direct mechanical coupling of the tines 4 and the membrane 5 exists. The plate 11, however, is preferably connected to the housing 3 or the outer edge of the membrane 5 in such a manner that there is essentially no mechanical coupling between the plate 11 and membrane 5. For such a purpose, the plate 11 also includes here a recessed portion, by which the plate 11 is located above the inner surfaces of the membrane 5.

Figure 3:
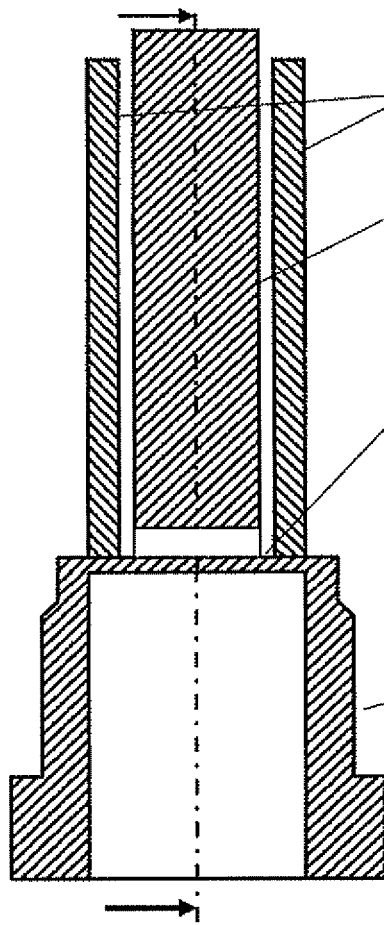
Figure 3:
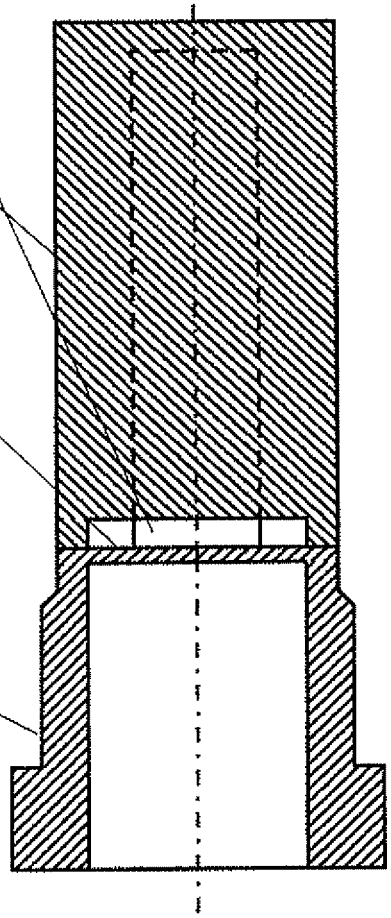

Two sections through the variant of FIG. 2 are presented in FIGS. 3 *a*) and *b*). How the plate 11 is arranged as a partition between both fork tines 4 is shown in FIG. 3 *a*). FIG. 3 *b*) is the section perpendicular to the dashed cutting plane shown in FIG. 3 *a*). It is seen that the plate 11 essentially has mechanical contact only with the edge of the membrane 5. Mechanical contact is prevented by the recessed portion of plate 11 above the inner surface of the membrane 5.

A further development is presented in FIGS. 4 *a*), *b*) and *c*), in which a pot like element 12 is provided above the plate 11. This pot like element 12 forms with the plate 11 the limiting element 10 and, in addition to the plate 11, limits the medium in the environment of the fork tines. Thus, the fork tines 4 are essentially framed by the limiting element 10. The limiting element 10 is open laterally so that the medium can reach the inner space and, thus, can also come in contact with the fork tines 4. A further section c), in which is seen that the pot like element 12 is here embodied essentially cylindrically, is presented beneath the lateral section a). In such case, the round cylinder, which forms the pot like element 12, in each case, exhibits a flattening of the radius where the element 12 faces the broad sides of the fork tines 4.

In order to noticeably increase the sensitivity the measuring, the pot like element 12 is spaced a small distance d from the fork tines 4, wherein the distance d is selected so that, on the one hand, the fork tines 4 of the pot like element 12 are not constrained during their oscillations and, on the other hand, the co-moving mass of the fork tines 4 is noticeably increased. In order to achieve this, the distance between the fork tines 4 and the pot like element 12 is preferably smaller than half the distance between the two fork tines 4.

Three other sections through an additional variant are presented in FIGS. 5 *a*), *b*) and *c*). The pot like element 12 is located here essentially only at the height of the ends of the fork tines facing away from the membrane 5, where paddles are most often located. As seen in FIG. 5 *b*), the pot like element 12 surrounds the tines and therewith also especially the paddles, not shown here, mounted on the ends of the tines. The paddles produce the enlarged interaction area. In an additional embodiment, the pot like element 12 is the single component of the limiting element. In an additional embodiment, the pot like element 12 does not surround the upper end of the fork tines, but instead the end facing the membrane. For this embodiment, the limiting element comprises essentially only a hollow cylinder. If, for example, a membrane oscillator is the subject, the limiting element comprises an embodiment of a type of raised lid, which has cavities for the flow of the medium.

LIST OF REFERENCE CHARACTERS

1 mechanically oscillatable unit
2 transducer unit
3 housing
4 fork tines
5 membrane
6 paddles
10 limiting element
11 plate
12 pot like element
20 medium
21 container

The invention claimed is:

1. An apparatus for determining and/or monitoring at least one process variable of a medium, comprising:
   at least one mechanically oscillatable unit, which at least partially comes in contact with the medium;
   at least one transducer unit, which excites said at least one mechanically oscillatable unit to execute mechanical oscillations and which receives mechanical oscillations from said at least one mechanically oscillatable unit;
   at least one housing; and
   at least one limiting element, wherein:
   said at least one limiting element is embodied and arranged in such a manner that said at least one limiting element at least partially surrounds said at least one mechanically oscillatable unit; and
   the resulting reduction of volume surrounding said at least one mechanically oscillatable unit increases measuring sensitivity of the apparatus, wherein:
   said at least one mechanically oscillatable unit has at least two fork tines;
   said at least one limiting element has at least one plate; and
   said at least one plate is arranged between said at least two fork tines of said at least one mechanically oscillatable unit.

2. The apparatus as claimed in claim 1, wherein:
   said at least one mechanically oscillatable unit has at least one membrane.

3. The apparatus as claimed in claim 2, wherein:
   said at least one limiting element is at least partially placed on an edge of said at least one membrane.

4. The apparatus as claimed in claim 1, wherein:
   said at least one mechanically oscillatable unit has at least one paddle.

5. The apparatus as claimed in claim 4, wherein:
   said inner space surrounds at least said paddle.

6. The apparatus as claimed in claim 1, wherein:
   said at least one limiting element has at least one pot like element having an inner space open on at least one side; and
   said inner space surrounds at least a part of said at least one mechanically oscillatable unit.

7. The apparatus as claimed in claim 1, wherein:
said at least one limiting element is embodied and connected to said at least one housing in such a manner that said at least one mechanically oscillatable unit is essentially free from direct mechanical contact with said at least one limiting element.

8. The apparatus as claimed in claim 1, wherein:
said at least one plate is embodied in such a manner and said at least one limiting element is connected to the edge of said at least one membrane in such a manner that said at least one membrane is free from direct mechanical contact with said at least one plate.

9. A limiting element in combination with an apparatus for determining and/or monitoring at least one process variable of a medium as defined in claim 1, wherein:
the apparatus has at least one mechanically oscillatable unit, which at least partially comes in contact with the medium; and at least one housing; and
the limiting element is embodied and is arrangeable relative to the mechanically oscillatable unit in such a manner that the limiting element at least partially surrounds the mechanically oscillatable unit and effects an increase of the measuring sensitivity of the apparatus.

10. The limiting element as claimed in claim 9, wherein:
the limiting element has at least one plate.

11. The limiting element as claimed in claim 10, wherein:
said at least one plate is embodied in such a manner and the limiting element is connectable with the edge of a membrane in such a manner that said membrane is free from direct mechanical contact with said plate.

12. The limiting element as claimed in claim 9, wherein:
the limiting element has at least one pot like element with an inner space open on at least one side.

13. The limiting element as claimed in claim 9, wherein:
the limiting element is embodied and connectable with said at least one housing in such a manner that the mechanically oscillatable unit is essentially free from direct mechanical contact with the limiting element.

14. The limiting element as claimed in claim 9, wherein:
the limiting element is placeable at least partially on an edge of a membrane.

* * * * *